United States Patent
Nagai et al.

(10) Patent No.: US 10,226,543 B2
(45) Date of Patent: Mar. 12, 2019

(54) ALLERGEN INACTIVATOR

(75) Inventors: Shinichi Nagai, Nagoya (JP); Takashi Sugiyama, Hatsukaichi (JP)

(73) Assignee: FUMAKILLA LIMITED, Tokyo (JP)

( * ) Notice: Subject to any disclaimer, the term of this patent is extended or adjusted under 35 U.S.C. 154(b) by 468 days.

(21) Appl. No.: 11/885,644

(22) PCT Filed: Mar. 17, 2006

(86) PCT No.: PCT/JP2006/305415
§ 371 (c)(1),
(2), (4) Date: Sep. 5, 2007

(87) PCT Pub. No.: WO2006/103960
PCT Pub. Date: Oct. 5, 2006

(65) Prior Publication Data
US 2008/0169447 A1    Jul. 17, 2008

(30) Foreign Application Priority Data
Mar. 25, 2005   (JP) .................................. 2005-089661

(51) Int. Cl.
| | | |
|---|---|---|
| *A01N 25/06* | (2006.01) | |
| *A61L 2/232* | (2006.01) | |
| *A01N 59/16* | (2006.01) | |
| *A61L 2/22* | (2006.01) | |
| *B01J 35/00* | (2006.01) | |
| *C09K 3/22* | (2006.01) | |
| *B01J 21/06* | (2006.01) | |
| *B01J 37/02* | (2006.01) | |

(52) U.S. Cl.
CPC ............. *A61L 2/232* (2013.01); *A01N 25/06* (2013.01); *A01N 59/16* (2013.01); *A61L 2/22* (2013.01); *B01J 35/004* (2013.01); *C09K 3/22* (2013.01); *B01J 21/063* (2013.01); *B01J 37/0219* (2013.01)

(58) Field of Classification Search
USPC ......................................................... 252/88.1
See application file for complete search history.

(56) References Cited

U.S. PATENT DOCUMENTS

| | | |
|---|---|---|
| 4,278,206 A | 7/1981 | Prussin |
| 4,806,526 A | 2/1989 | Green et al. |
| 4,977,142 A | 12/1990 | Green et al. |
| 5,468,471 A | 11/1995 | Zecchino et al. |
| 5,811,192 A | 9/1998 | Takahama et al. |
| 6,482,357 B1 | 11/2002 | Fox et al. |
| 6,800,247 B1 | 10/2004 | Suh et al. |
| 2003/0203035 A1 | 10/2003 | Hasan et al. |
| 2003/0236317 A1 | 12/2003 | Sakatani et al. |
| 2004/0033269 A1 | 2/2004 | Hei et al. |
| 2004/0211728 A1* | 10/2004 | Liu et al. ..................... 210/645 |
| 2005/0227859 A1* | 10/2005 | Nakabayashi et al. ....... 502/150 |

FOREIGN PATENT DOCUMENTS

| | | | |
|---|---|---|---|
| CN | 1160027 A | | 9/1997 |
| CN | 1582662 | * | 2/2005 |
| CN | 1582662 A | | 2/2005 |
| CN | 1596987 A | | 3/2005 |
| EP | 0937398 | * | 2/1999 |
| EP | 0925846 A2 | | 6/1999 |
| EP | 0 937 398 A1 | | 8/1999 |
| EP | 1375602 A1 | | 1/2004 |
| GB | 2058820 A | | 4/1981 |
| GB | 2 329 586 A | | 3/1999 |
| GB | 2358638 A | | 8/2001 |
| JP | 2-16731 B2 | | 4/1990 |
| JP | 8-165208 A | | 6/1996 |
| JP | 09025439 | * | 6/1996 |
| JP | 10204335 | * | 8/1998 |
| JP | 11-315398 A | | 11/1999 |
| JP | 11-349423 A | | 12/1999 |
| JP | 2000-15032 A | | 1/2000 |
| JP | 2001-172019 A | | 6/2001 |
| JP | 3218021 | * | 10/2001 |
| JP | 2002-119818 A | | 4/2002 |
| JP | 2002-519185 A | | 7/2002 |
| JP | 2002355299 A | * | 12/2002 .............. A61L 9/00 |
| JP | 2004-510841 A | | 4/2004 |
| JP | 2004-324241 A | | 11/2004 |
| JP | 2005-54154 A | | 3/2005 |
| JP | 2005-278781 A | | 10/2005 |
| JP | 2006-57212 A | | 3/2006 |
| WO | WO 94/18940 A1 | | 9/1994 |
| WO | WO 02/28179 A1 | * | 4/2002 .............. A01N 25/10 |
| WO | WO 2002/28179 | * | 4/2002 .............. A01N 25/10 |

OTHER PUBLICATIONS

English language abstract of JP 2000-016941 (Jan. 18, 2000).
English language abstract of JP 2002-128680 (May 9, 2002).
English language abstract of JP 2002-167332 (Jun. 11, 2002).
English language abstract of JP 2000-063207 (Feb. 29, 2000).
English language abstract of JP 2000-264837 (Sep. 26, 2000).
English language abstract of JP 2001-335474 (Dec. 4, 2001).
English language abstract of JP 2000-015032 (Jan. 18, 2000).
English language abstract of JP 11-315398 (Nov. 16, 1999).
English language abstract of JP 2005-278781 (Oct. 13, 2005).
Chinese Office Action dated Jan. 8, 2010 in corresponding Chinese Application No. 2006800096597 with English translation.
Taiwanese Office Action dated Dec. 28, 2011 for Application No. 095110470.

(Continued)

*Primary Examiner* — Monique R Peets
(74) *Attorney, Agent, or Firm* — Birch, Stewart, Kolasch & Birch, LLP (57) ABSTRACT

There is provided an allergen inactivating agent having less lowering in performance due to fluctuation in pH, and being capable of not only adsorbing and removing an allergen, but also inactivating and removing the allergen itself. In addition, there is provided a house dust treatment agent, spray, and sheet, capable of effectively removing house dust, without any disadvantages upon use such as generation of stains.

25 Claims, 2 Drawing Sheets

(56) References Cited

OTHER PUBLICATIONS

Office Action and Search Report for corresponding Chinese Patent Application No. 201110094070.4, dated Jan. 28, 2013.
European Search Report dated Jul. 19, 2011 for Application No. 11168706.7.
Office Action (European Patent Office Summons to Attend Oral Proceedings Pursuant to Rule 115(1) EPC) issued in the corresponding European Patent Application No. 11168706.7 dated Dec. 10, 2015.
Japanese Office Action, dated Nov. 12, 2015, for Japanese Application No. 2012-29719.

* cited by examiner

ALLERGEN INACTIVATOR

TECHNICAL FIELD

The present invention relates to an allergen inactivating agent which acts on an allergen in house dust, and further to a house dust treatment agent which facilitates aggregation and removal of the house dust in which the allergen is inactivated.

BACKGROUND ART

In a room, there are various kinds of house dust such as dead mites, feces, pollens, dust, and flocks. In general, the room is cleaned with a vacuum cleaner or the like. However, fine house dust such as those entwined to carpets, sofas, or beddings cannot be sufficiently removed by simply vacuuming with the vacuum cleaner or the like. The onset of various allergic diseases such as asthma, dermatitis, and pollinosis have been known to be caused by an allergen contained in house dust, mainly a mite allergen or a pollen. Therefore, it is important to inactivate the allergen and to remove house dust.

As techniques for effectively removing an allergen, there have been known, for example, a technique of treatment with a water-swellable clay, polyvinyl alcohol, or the like (see, for example, Patent Publications 1 and 2); a technique of treatment with an inorganic powder such as kaolin or talc (see Patent Publication 3); and the like. Any of these techniques comprises removing an allergen by adsorption with each of the components used. In addition, a technique of treatment with tannic acid, an alcohol, or a benzalkonium chloride, and other techniques (see Patent Publications 4 to 7) have been known. These techniques comprise removing an allergen by denaturation and inactivation.

Patent Publication 1: Japanese Patent Laid-Open No. 2000-16941
Patent Publication 2: Japanese Patent Laid-Open No. 2002-128680
Patent Publication 3: Japanese Patent Laid-Open No. 2002-167332
Patent Publication 4: Japanese Examined Patent Publication No. Hei 2-16731
Patent Publication 5: Japanese Patent Laid-Open No. 2000-63207
Patent Publication 6: Japanese Patent Laid-Open No. 2000-264837
Patent Publication 7: Japanese Patent Laid-Open No. 2001-335474

DISCLOSURE OF THE INVENTION

Problems to be Solved by the Invention

However, some of the techniques for removing an allergen by adsorption as mentioned above have the tendency of lowering the adsorbability at high pHs. In addition, some components used in the technique for removing an allergen by denaturation and inactivation as mentioned above have a disadvantage in usability such as generation of stains on an object to be treated. Furthermore, none of the techniques described above do not yet have a satisfactory effect of removing house dust.

Therefore, an object of the present invention is to provide an allergen inactivating agent having less lowering in performance due to fluctuation in pH, and being capable of not only adsorbing and removing an allergen, but also inactivating and removing the allergen itself. Another object of the present invention is to provide a house dust treatment agent, spray, and sheet, capable of effectively removing house dust, without any disadvantages in use such as generation of stains.

Means to Solve the Problems

Specifically, the present invention relates to:

[1] an allergen inactivating agent containing a titanium oxide having a photocatalytic activity;
[2] a house dust treatment agent containing the allergen inactivating agent of the above [1] and sodium polyacrylate;
[3] a spray for treating house dust comprising a spray container filled with the house dust treatment agent of the above [2];
[4] a sheet for treating house dust comprising a sheet material impregnated with the house dust treatment agent of the above [2];
[5] use of a titanium oxide having a photocatalytic activity, for inactivating an allergen; and
[6] a method for producing a house dust treatment agent, including the step of dispersing a titanium oxide having a photocatalytic activity and sodium polyacrylate in water, a lower alcohol or a mixture thereof.

Effects of the Invention

According to the present invention, there can be provided an allergen inactivating agent having less lowering in performance due to fluctuation in pH, and being capable of not only adsorbing and removing an allergen, but also inactivating and removing the allergen itself. In addition, according to the present invention, there can be provided a house dust treatment agent, spray, and sheet, capable of effectively removing house dust, without any disadvantages in use such as generation of stains.

BEST MODE FOR CARRYING OUT THE INVENTION

One feature of the allergen inactivating agent of the present invention resides in that the allergen activating agent contains a titanium oxide having a photocatalytic activity. Since the allergen inactivating agent has the feature, there are exhibited some effects that not only the allergen can be adsorbed and removed by utilization of the allergen adsorbability of the titanium oxide, but also the allergen can be inactivated and removed by the photocatalytic activity of the titanium oxide. In addition, since the titanium oxide contained in the allergen inactivating agent of the present invention is a metallic oxide, the titanium oxide does not discolor with the passage of time, so that the stain or the like which has conventionally been a disadvantage is less likely to be generated.

The allergen to be inactivated by the allergen inactivating agent of the present invention includes dead mites, feces, pollens, and the like.

The term "photocatalytic activity" used herein refers to an ability of degrading an organic substance or the like by utilizing oxidation power exhibited by light energy. Whether or not a titanium oxide has the photocatalytic activity can be confirmed by, for example, whether or not fading of methylene blue is caused by the titanium oxide. Specifically, the photocatalytic activity can be confirmed by adding a titanium oxide to an aqueous solution of methylene blue, and visually observing the extent of fading of the methylene blue while subjecting to photoirradiation.

The crystal form of the titanium oxide used in the present invention includes an anatase type and a rutile type, and the anatase type is preferable, from the viewpoint of the allergen inactivating property.

The average particle size of the primary particle of the titanium oxide used in the present invention is not particularly limited. The average particle size is preferably from 1 to 200 nm, more preferably from 1 to 30 nm, and even more preferably from 5 to 20 nm, from the viewpoint of the allergen inactivating property. When the average particle size of the titanium oxide is within this range, the allergen inactivating agent is desirably likely to have enhanced effects of inactivating and removing an allergen, and also to have enhanced dispersion stability of the titanium oxide. When the primary particle of the titanium oxide has an average particle size of, for example, about several hundred nanometers, the average particle size can be determined with an electron microscope. When the primary particle of the titanium oxide has the above average particle size or less, the average particle size can be determined as a crystallite size by using the Scherrer's formula known in the art from the determination results of the X-ray analysis. The average particle size of the primary particle of the titanium oxide can be easily adjusted, for example, by calcinating the titanium oxide. The titanium oxide can also be used by mixing one or more kinds having different average particle sizes.

The content of the titanium oxide in the allergen inactivating agent of the present invention is not particularly limited, as long as the effects of the present invention are exhibited. The content is preferably from 0.005 to 100% by weight, and more preferably from 0.01 to 20% by weight.

The solvent used in the allergen inactivating agent is preferably water, a lower alcohol or a mixture thereof. As the water, for example, a purified water or the like can be used. The number of carbon atoms of the lower alcohol is preferably from 1 to 5, more preferably from 1 to 4, and even more preferably 2, from the viewpoint of the dispersion stability of the titanium oxide. Therefore, among the lower alcohols, ethanol is preferable.

When a mixed solution of water and a lower alcohol is used as a solvent, the weight ratio of the water to the lower alcohol is preferably from 50:50 to 80:20, and more preferably from 60:40 to 70:30, from the viewpoint of enhancing dryness and usability of the house dust treatment agent, and from the viewpoint of reducing flammability and of alleviating irritability.

The allergen inactivating agent of the present invention may contain a proper amount of a dispersant, from the viewpoint of enhancing dispersibility of the titanium oxide. The amount of the dispersant cannot be unconditionally determined because the amount differs depending upon its kinds or the like. Therefore, it is preferable that the amount of the dispersant is adjusted according to its kinds or the like within the range that would not hinder the object of the present invention.

The allergen inactivating agent of the present invention may further contain a proper amount of an additive such as a deodorant, an insecticide, a miticide, a repellent, a bactericide, a mildewproof preservative, an antistatic agent, a brightener, a stabilizer, a perfume, a pH adjusting agent, or a texture improver. The amount of the additive cannot be unconditionally determined because the amount differs depending upon its kinds or the like. Therefore, it is preferable that the amount of the additive is adjusted according to the kind or the like within the range that would not hinder the object of the present invention.

The allergen inactivating agent of the present invention can be used in the form of a dispersion prepared, for example, by dispersing a titanium oxide in the above-mentioned solvent, or the titanium oxide per se can be used as an allergen inactivating agent.

The allergen inactivating agent of the present invention can exhibit its effects in a wide range of pHs. The pH is preferably from 4 to 9, from the viewpoint of maintaining the allergen inactivating action.

The house dust treatment agent, spray, and sheet of the present invention containing the above-mentioned allergen inactivating agent will be sequentially explained hereinbelow.

(1) Treatment Agent

An object to be treated with the house dust treatment agent of the present invention is not particularly limited, as long as it is generally called house dust. The house dust treatment agent exhibits an excellent removing effect on house dust containing an allergen such as dead mites, feces, or pollens, and exhibits especially an excellent removing effect on house dust containing a mite allergen such as dead mites and feces.

The house dust treatment agent of the present invention can be used as it is, and is preferably used in the preparation of the spray and sheet described later.

The content of the allergen inactivating agent contained in the house dust treatment agent is not particularly limited, as long as the effects of the present invention are exhibited. The content of the allergen inactivating agent, in terms of the titanium oxide, is preferably 0.005 to 20% by weight, more preferably from 0.01 to 1% by weight, and even more preferably from 0.01 to 0.2% by weight, from the viewpoint of securing sufficient dispersibility of the titanium oxide in the solvent, and exhibiting sufficient removing effects on the house dust.

The house dust treatment agent further contains sodium polyacrylate. Since the house dust treatment agent contains the component, the house dust treatment agent exhibits additional effects of, for example, aggregating house dust, thereby facilitating removal of the house dust with a vacuum cleaner or the like.

The sodium polyacrylate used in the present invention has a weight-average molecular weight of preferably from $200\times10^4$ to $2000\times10^4$, and more preferably from $500\times10^4$ to $1000\times10^4$.

The content of the sodium polyacrylate in the house dust treatment agent of the present invention is not particularly limited. The content is preferably from 0.0001 to 5% by weight, more preferably from 0.0005 to 1% by weight, and even more preferably from 0.0005 to 0.1% by weight.

As the solvent used in the house dust treatment agent, the water, a lower alcohol or a mixture thereof contained in the allergen inactivating agent may be used as the solvent for the house dust treatment agent. Alternatively, a freshly added water, a lower alcohol or a mixture thereof may be used as the solvent for the house dust treatment agent. As the water, a purified water or the like can be used, in the same manner as in the allergen inactivating agent. The number of carbon atoms of the lower alcohol is preferably from 1 to 5, more preferably from 1 to 4, and even more preferably 2, from the viewpoint of dispersion stability of the titanium oxide, in the same manner as in the allergen inactivating agent. Therefore, among the lower alcohols, ethanol is preferable.

When a mixed solution of water and a lower alcohol is used as a solvent, the weight ratio of the water to the lower alcohol is preferably from 50:50 to 80:20, and more preferably from 60:40 to 70:30, from the viewpoint of enhancing dryness and usability of the house dust treatment agent, and from the viewpoint of reducing flammability and of alleviating irritability.

The total content of the water and the lower alcohol in the house dust treatment agent is determined in consideration of the dispersion stability of the titanium oxide, and the dryness and usability of the house dust treatment agent. It is preferable that the total content of the water and the lower alcohol mentioned above is usually the balance of the titanium oxide, the sodium polyacrylate, the additive, and the deodorant component.

The house dust treatment agent of the present invention may contain a proper amount of an additive such as a dispersant, an insecticide, a miticide, a repellent, a bactericide, a mildewproof preservative, an antistatic agent, a brightener, a stabilizer, a perfume, a pH adjusting agent, or a texture improver. The amount of the additive cannot be unconditionally determined because the amount differs depending upon the kind or the like. Therefore, it is preferable that the amount of the additive is adjusted according to the kind or the like within the range that would not hinder the object of the present invention.

It is preferable that the house dust treatment agent of the present invention further contains a deodorant component. Since the house dust treatment agent contains the component, the house dust treatment agent can further exhibit an additional effects, for example, of removing odors derived from human sebum and sweat.

The deodorant component is not particularly limited, and includes, for example, extracts from plants such as green tea, persimmon, bamboo, camellia, rose, chrysanthemum, pine, red cedar (*Cryptomeria japonica*), plantain, sugar cane (*Saccharum officinarum*), and *Phyllostachys pubescens*; essential oils of plants such as rose oil, lavender oil, bergamot oil, bitter almond oil, cananga oil, cassia oil, cedar wood oil, cinnamon oil, citronella oil, lemon oil, lime oil, nutmeg oil, peppermint oil, abies oil, pine oil, star anise oil, turpentine oil, vetiver oil, eucalyptus oil, rosemary oil, and *hinoki* cypress oil; components derived from essential oils of plants such as anethol, citronellal, citral, limonene, cineole, α-pinene, and terpinolene; and deodorant components such as methyl methacrylate, ethyl methacrylate, lauryl methacrylate, stearyl methacrylate, ethyl pyruvate, pyruvic esters, dimethyl maleate, and betaine; and the like. The extracts from plants such as green tea, persimmon, and bamboo are preferable because of the excellent effect of removing odors as mentioned above.

The content of the deodorant component in the house dust treatment agent of the present invention is not particularly limited, as long as the effect of the present invention is exhibited. The content is preferably from 0.01 to 10% by weight, and more preferably from 0.05 to 2% by weight, from the viewpoint of exhibiting sufficient effects of removing odors.

As the house dust treatment agent, for example, a house dust treatment agent containing 0.01 to 0.2% by weight of a titanium oxide, 0.0005 to 0.01% by weight of sodium polyacrylate, 0.01 to 5% by weight of an additive, 20 to 50% by weight of ethanol, and the balance water is especially preferable.

The house dust treatment agent of the present invention is obtained by properly mixing each of the components mentioned above. Since titanium oxide is generally less likely to be dispersed in water, it is usually preferable that a dispersant is added to water, a lower alcohol or a mixture thereof, while stirring to prepare a dispersion.

The house dust treatment agent of the present invention can exhibit its effect in a wide range of pHs. The pH is preferably from 4 to 9, from the viewpoint of maintaining the allergen inactivating action.

(2) Spray

The spray of the present invention comprises a known spray container filled with the above-mentioned house dust treatment agent, and a spray container filled with a house dust treatment agent of a preferred embodiment is more preferable.

The kinds of the spray container are not particularly limited. For example, a spray container with triggering system, a pump spray container, an accumulator spray container or the like is preferable, from the viewpoint of convenience of use. The capacity of the spray container usually is preferably from about 10 to about 1000 mL, more preferably from about 30 to about 750 mL, and even more preferably from about 50 to about 500 mL, from the viewpoint of usability or the like.

The spray container can be filled with the above-mentioned house dust treatment agent according to a known method.

(3) Sheet

The sheet of the present invention comprises a known sheet material impregnated with the above-mentioned house dust treatment agent, and a sheet material impregnated with a house dust treatment agent of a preferred embodiment is more preferable.

The content of ethanol in an especially preferred embodiment of the above-mentioned house dust treatment agent is from 20 to 50% by weight. However, when the above-mentioned house dust treatment agent is used for the preparation of a sheet, the content of ethanol in the especially preferred embodiment is from 1 to 50% by weight in consideration of an influence on a flooring wax, or the like.

The shape of the sheet is not particularly limited. Usually, the sheet having a length of about 150 to about 200 mm, a width of about 200 to about 300 mm, and a thickness of about 0.05 to about 1 mm is preferable. The sheet may be made of a single layer or laminated with layers formed of the same material or different materials.

The above-mentioned sheet material is not particularly limited, and includes, for example, nonwoven fabric, woven fabric, paper and the like. The nonwoven fabric is preferable from the viewpoint of its high strength, low cost and easy adjustment of the basis weight. These sheet materials can be produced in accordance with known methods. In addition, commercially available products may be used if available.

For example, the above-mentioned nonwoven fabric suitably used as a sheet material can be produced by a known method such as chemical bond method, thermal bond method, span lace method, span bond method, or needle punch method. In addition, the material therefor is not particularly limited, and includes, for example, polypropylene, polyethylene, polyester, acrylic, rayon, cotton, pulp, and the like. As the material for the nonwoven fabric, the rayon or pulp is preferable from the viewpoint of facilitation of impregnation of the house dust treatment agent, and the polyethylene or polyester is preferable from the viewpoint of keeping the strength. Further, from the both viewpoints, a blended fabric in which ones exemplified as the preferred materials are blended in a proper ratio is more preferable.

The nonwoven fabric having a basis weight, i.e., a fabric weight per unit area, of usually from about 30 to about 80 $g/m^2$ is preferable.

The sheet material can be impregnated with the above-mentioned house dust treatment agent in accordance with a known method. For example, in a case where a sheet material comprising a nonwoven fabric having a basis weight within the above-mentioned preferred range is impregnated with the above-mentioned house dust treatment agent, it is preferable that the sheet material is immersed in the above-mentioned house dust treatment agent having a volume two or three times or so larger than the basis weight of the sheet material to impregnate the sheet material with the above-mentioned house dust treatment agent. Specifically, when the basis weight is 50 $g/m^2$, it is preferable the sheet material comprising a nonwoven fabric is impregnated with 100 to 150 g of the above-mentioned house dust treatment agent, per 1 $m^2$ of the sheet material.

The house dust treatment agent and spray of the present invention may be used by applying the agent by means of, for example, sprinkling or the like to interior carpet, sofa, bedding or the like which is an object to be cleaned with a vacuum cleaner. In this case, immediately after the application, or preferably after allowing the object to stand for a period of from several minutes to several hours, the above-mentioned object is cleaned in a usual manner with a vacuum cleaner, so that an allergen can be effectively inactivated, and that house dust can be effectively removed. In addition, for example, the house dust treatment agent and spray can be applied on bedding or the like before airing out the bedding or the like. In that case, after a given period of airing, house dust can be effectively removed by beating the bedding or the like with a duster or hand before taking in the bedding or the like indoors. Usually, adhered house dust is finely pulverized upon beating of aired bedding or the like, whereby the dust may become even more difficult to be removed in some cases. However, if the house dust treatment agent or the like of the present invention is applied in advance, the house dust is aggregated, so that the house dust can be effectively removed.

Since the house dust treatment agent is not easily sprinkled or the like, it is preferable that the house dust treatment agent is used in the form of a spray. In addition, the spray is preferably used in a state that titanium oxide is homogeneously dispersed, from the viewpoint of sufficiently exhibiting the action of inactivating an allergen and the effects of removing house dust. Therefore, it is preferable that the spray usually is well shaken before application to the object. Further, upon the application, since the object is wet in a part where the spray is applied, it is preferable that the object is allowed to stand for a given period of time after the application to adequately dry the object, and the dried object is then cleaned. When the house dust treatment agent or the like of the present invention contains a deodorant component containing an extract from plants such as green tea, persimmon or bamboo, the allergen can be effectively inactivated, so that the house dust can be effectively removed, and at the same time the odors as mentioned above can be effectively removed.

On the other hand, the sheet of the present invention is preferably used for wiping a part on which house dust is accumulated, for example, surface of bedding, a shade of an interior lamp, a window frame, floor or the like. Usually, when the part is cleaned with a damp cloth, the house dust merely gets wet, but it is still difficult to wipe off the house dust. According to the sheet of the present invention, not only the allergen can be effectively inactivated but also house dust can be aggregated and effectively removed. In addition, if the deodorant component as mentioned above is contained, the odor as mentioned above can also be removed effectively.

EXAMPLES

Examples 1 to 5 and Comparative Examples 1 to 3

Preparation of Allergen Inactivating Agent

Each component of titanium oxides A to F listed in Table 1, silica or talc were mixed in accordance with the amount listed in Table 2, to give test solutions 1 to 5 (Examples 1 to 5) and comparative test solutions 1 to 3 (Comparative Examples 1 to 3).

Titanium oxide and optionally silica or talc were dispersed in water by adding each of the components in a small amount at a time to water having a normal temperature under stirring. In order to confirm the photocatalytic activity of titanium oxide used, 0.1 g of a titanium oxide was added to 100 mL of an aqueous methylene blue solution (0.1% by weight) while stirring, and the resulting dispersion was taken with a medicine dropper. One drop of the dispersion was put on a slide glass, and the extent of fading of the methylene blue was observed with naked eyes while subjecting to photoirradiation (black light, ultraviolet ray intensity: 1000 $\mu W/cm^2$). After one hour from the beginning of the photoirradiation, the color of the dispersion in which each of the titanium oxides A to E was dispersed was changed from blue to colorless transparent, while the color of the dispersion in which the titanium oxide F was dispersed showed no change in color from blue. Therefore, the titanium oxides A to E had a photocatalytic activity, while the titanium oxide F did not have a photocatalytic activity.

TABLE 1

|  | Particle Size (nm) | Crystal Form |
| --- | --- | --- |
| Titanium Oxide A | 6 | Anatase |
| Titanium Oxide B | 7 | Anatase |
| Titanium Oxide C | 20 | Anatase |
| Titanium Oxide D | 30 | Anatase |
| Titanium Oxide E | 180 | Anatase |
| Titanium Oxide F | 250 | Rutile |

TABLE 2

|  |  | Example | | | | | Comparative Example | | |
| --- | --- | --- | --- | --- | --- | --- | --- | --- | --- |
|  |  | 1 | 2 | 3 | 4 | 5 | 1 | 2 | 3 |
| Titanium Oxide (g) | A | 0.1 | — | — | — | — | — | — | — |
|  | B | — | 0.1 | — | — | — | — | — | — |
|  | C | — | — | 0.1 | — | — | — | — | — |
|  | D | — | — | — | 0.1 | — | — | — | — |
|  | E | — | — | — | — | 0.1 | — | — | — |
|  | F | — | — | — | — | — | 0.1 | — | — |
| Silica (g) |  | — | — | — | — | — | — | 0.1 | — |
| Talc (g) |  | — | — | — | — | — | — | — | 0.1 |
| Water (g) |  | 99.9 | 99.9 | 99.9 | 99.9 | 99.9 | 99.9 | 99.9 | 99.9 |
| Total (g) |  | 100 | 100 | 100 | 100 | 100 | 100 | 100 | 100 |

Test Example 1

Evaluation of Allergen Inactivating Action

The allergen inactivating action of each of the test solutions 1 to 5 and the comparative test solutions 1 to 3 mentioned above was evaluated using a mite allergen as an allergen in accordance with the following method.

The amount 0.15 mL each of the test solutions 1 to 5 and the comparative test solutions 1 to 3 was added to 1 mL of an antigen solution prepared by dissolving a Dfb antigen [crude antigen of mite body; obtained by the method proposed by Sasa, M. et al. (*Jpn. J. Exp. Med.*, 40: 367-382, 1970)] in PBS so as to have a concentration of 20 µg/mL. As a negative control, the same volume of water was added in place of the test solution. The mixture was allowed to stand at room temperature for, 2 hours under a fluorescent lamp (36 W×8), and thereafter the extent of allergen inactivating action by each test solution was determined with a MITEY CHECKER (mite allergen detection kit: manufactured by Shinto Fine Co., Ltd.).

According to the MITEY CHECKER, the amount of a mite allergen Der2 (one of the major allergens), capable of acting as an allergen, in the solution to be tested, can be determined by a horizontal development process using a monoclonal antibody. Therefore, it is thought that the extent of allergen inactivating action by each test solution means an action of inactivating allergens in each test solution.

Table 3 below shows the criteria of judgment on the amount of mite allergen by the MITEY CHECKER, and Table 4 shows the judgment results of the extent of allergen inactivating action by each test solution based on the criteria of judgment.

TABLE 3

| Judgment | Amount of Mite Allergen |
| --- | --- |
| ++ | >3.5 µg/mL (equivalent to ">35 mites/mL") |
| + | 1.0 µg/mL (equivalent to 10 mites/mL) |
| ± | 0.5 µg/mL (equivalent to 5 mites/mL) |
| − | <0.1 µg/mL (equivalent to "<1 mite/mL") |

TABLE 4

|  | Test Solution | | | | | Comparative Test Solution | | | Negative |
| --- | --- | --- | --- | --- | --- | --- | --- | --- | --- |
|  | 1 | 2 | 3 | 4 | 5 | 1 | 2 | 3 | Control |
| Judgment | ± | ± | ± | ± | + | ++ | ++ | ++ | ++ |

It can be seen from Table 4 that the extent of allergen inactivating action by each of the test solutions 1 to 5 is higher than that by each of the comparative test solutions 1 to 3 and the negative control. The components used in the comparative test solutions are those used in the conventional technique for removing allergens. The results of Table 4 show that the extent of mite allergen inactivating action by the titanium oxide used in the present invention is especially excellent, as compared to these components.

Test Example 2

Influence of Light on Allergen Inactivating Action

The extent of allergen inactivating action was evaluated in the same manner as in Test Example 1, except that the light conditions were changed, in order to confirm how the allergen inactivating action of the test solution 1 mentioned above was influenced by light. As a control, the comparative test solution 1 was used. The results are shown in Table 5.

TABLE 5

|  | Under Indoor Fluorescent Lamp (36 W × 8) (15 µW/cm$^2$) | Outdoors (300 µW/cm$^2$) | Outdoors (2600 µW/cm$^2$) |
| --- | --- | --- | --- |
| Test Solution 1 | ± | − | − |
| Comparative Test Solution 1 | ++ | ++ | ++ |

According to Table 5, the extent of allergen inactivating action by the test solution 1 was further improved by exposing the test solution 1 to more intensive light, while, by contrast, the extent of allergen inactivating action by the comparative test solution 1 remained low regardless of the light conditions.

Test Example 3

Influence of pH on Allergen Inactivating Action

The extent of allergen inactivating action was evaluated in the same manner as in Test Example 1, except that the pH of the test solution was adjusted with lactic acid or sodium carbonate before the test, in order to confirm how the allergen inactivating action of the test solution 1 mentioned above was influenced by pH. The results are shown in Table 6.

Here, the test solution 1 before the test had a pH of 6.

TABLE 6

|  | pH | | | | | |
|---|---|---|---|---|---|---|
|  | 4 | 5 | 6 | 7 | 8 | 9 |
| Test Solution 1 | ± | ± | ± | ± | ± | ± |

It can be seen from Table 6 that the extent of allergen inactivating action by the test solution 1 is maintained regardless of the pH.

Example 6 and Comparative Examples 4 to 11

Preparation of House Dust Treatment Agent

Each component was mixed in accordance with the amount listed in Table 7, to give a test solution 6 (Example 6) and comparative test solutions 4 to 11 (Comparative Examples 4 to 11). Here, the unit used in Table 7 is gram.

TABLE 7

|  | Example | Comparative Example | | |
|---|---|---|---|---|
|  | 6 | 4 | 5 | 6 |
| Titanium Oxide A | 0.18 | 0.18 | 0.18 | 0.18 |
| Sodium Polyacrylate | 0.0045 | — | — | — |
| Sodium Alginate | — | 0.0045 | 0.09 | — |
| Potato Starch | — | — | — | 0.0045 |
| Polyvinyl Alcohol | — | — | — | — |
| Methylcellulose | — | — | — | — |
| Water | 270 | 270 | 270 | 270 |
| Ethanol | 180 | 180 | 180 | 180 |

|  | Comparative Example | | | | |
|---|---|---|---|---|---|
|  | 7 | 8 | 9 | 10 | 11 |
| Titanium Oxide A | 0.18 | 0.18 | 0.18 | 0.18 | 0.18 |
| Sodium Polyacrylate | — | — | — | — | — |
| Sodium Alginate | — | — | — | — | — |
| Potato Starch | 0.45 | — | — | — | — |
| Polyvinyl Alcohol | — | 0.0045 | 0.45 | — | — |
| Methylcellulose | — | — | — | 0.0045 | 0.45 |
| Water | 270 | 270 | 270 | 270 | 270 |
| Ethanol | 180 | 180 | 180 | 180 | 180 |

Test Example 4

Evaluation of Allergen Inactivating Action

The allergen inactivating action was evaluated for the test solution 6 and the comparative test solutions 4 to 11 in the same manner as in Test Example 1. The results are shown in Table 8.

Test Example 5

Evaluation of Hose Dust Aggregating Effect

As dust, 10 mg of standard dust [Cotton linter, manufactured by Japan Air Cleaning Association] was put into a plastic petri dish having a diameter of 9 cm, and 0.7 mL of each of the test solution 6 and the comparative test solutions 4 to 11 charged in a commercially available hand spray container was sprayed to the standard dust. After drying the sprayed mixture at room temperature, the respective sprayed dust was observed with a stereo microscope (manufactured by Nikon Corporation; magnification: 50 times) for the extents of adsorption and aggregation of the standard dust in accordance with the following evaluation criteria. As controls, one in which only the standard dust is placed in a plastic plate, and one in which water is sprayed in place of the test solution to the standard dust was placed in a plastic petri dish were prepared and observed in the same manner. The results are shown in Table 8.

<Adsorption and Aggregation of Standard Dust>

○: There are adsorption and aggregation.

×: There is no adsorption or aggregation.

Figure 1:
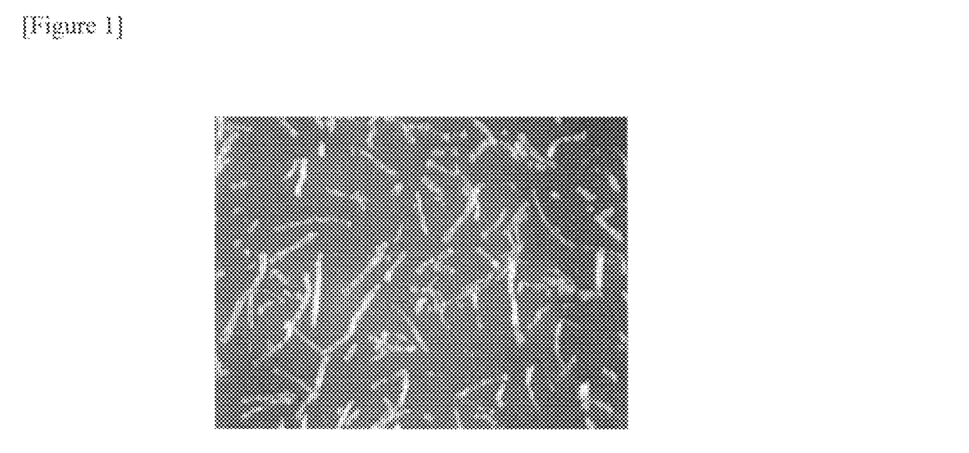
FIG. 1 A stereo micrograph (magnification: 50 folds) of standard dust.
Figure 2:
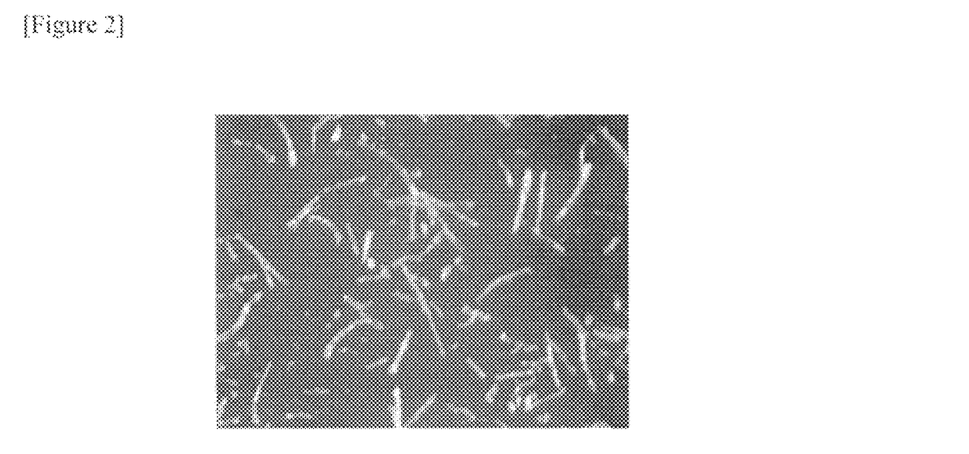
FIG. 2 A stereo micrograph (magnification: 50 folds) showing the state in which there is no adsorption or aggregation.
Figure 3:
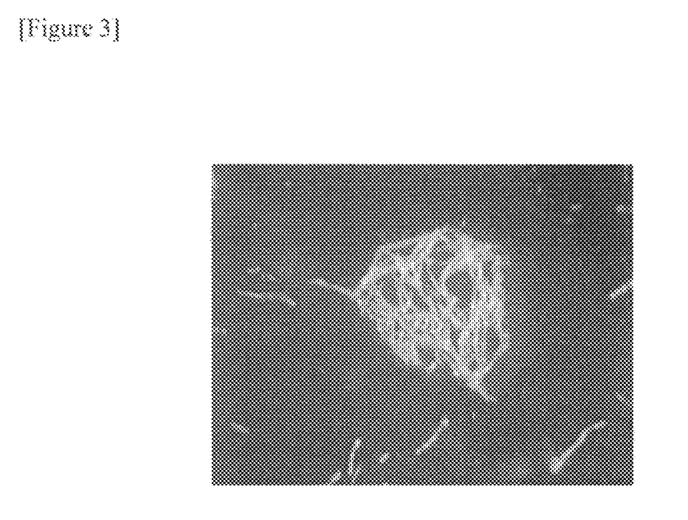
FIG. 3 A stereo micrograph (magnification: 50 folds) showing the state in which there are adsorption and aggregation.

Here, the adsorption and aggregation of the standard dust were evaluated by observing the adsorbed and aggregated states of the respective standard dust while the controls were considered to have no adsorption or aggregation. FIG. 1 shows a stereo micrograph of the standard dust, and FIGS. 2 and 3 show stereo micrographs of each evaluation (× or ○).

TABLE 8

|  | Test Solution | Comparative Test Solution | | | | | | | |
|---|---|---|---|---|---|---|---|---|---|
|  | 6 | 4 | 5 | 6 | 7 | 8 | 9 | 10 | 11 |
| Allergen Inactivating Action | ± | ± | + | ± | + | ± | + | ± | + |
| Adsorption and Aggregation of House Dust | ○ | X | ○ | X | ○ | X | ○ | X | ○ |

|  | Control | |
|---|---|---|
|  | Untreated | Treated with Water |
| Allergen Inactivating Action Adsorption and Aggregation of House Dust | X | X |

According to the results of Table 8, in the comparative test solution using sodium alginate, potato starch, polyvinyl alcohol, or methylcellulose as an aggregating agent, when the mixing ratio of the component was about 0.001% by weight (Comparative Examples 4, 6, 8, and 10), the adsorption or aggregation to the standard dust was not found (FIG. 2), and when the mixing ratio was increased in order to exhibit adsorption and aggregation to the standard dust (Comparative Examples 5, 7, 9, and 11), the allergen inactivating action of the titanium oxide was inhibited. On the contrary, in the test solution using sodium polyacrylate (Example 6), even when the component had a low concentration of about 0.001% by weight, the adsorption or aggregation to the standard dust was found (FIG. 3), and the allergen inactivating action was not inhibited.

INDUSTRIAL APPLICABILITY

According to the present invention, there can be provided an allergen inactivating agent, capable of effectively inactivating an allergen, a house dust treatment agent, spray, and sheet, capable of effectively removing house dust.

The invention claimed is:

1. A method for inactivating an allergen comprising applying to a house dust containing the allergen a composition, so that the allergen are inactivated, wherein
the composition consists of particles consisting of a titanium oxide having a photocatalytic activity, and optionally water, a lower alcohol, a mixture thereof, or sodium polyacrylate,
the titanium oxide consists of an anatase crystal form and 1 to 30 nm of an average primary particle size, and
the allergen is one or more selected from the group consisting of dead mites, feces of mites and pollens, and
wherein the composition does not include a titanium oxide having a rutile crystal form.

2. The method according to claim 1, wherein the composition consists of the particles consisting of the titanium oxide, and further the water, the lower alcohol or the mixture thereof.

3. The method according to claim 1 or 2, wherein the composition consists of the particles consisting of the titanium oxide, and sodium polyacrylate.

4. The method according to claim 1, wherein the titanium oxide is contained in an amount of 0.005 to 20% by weight.

5. The method according to claim 2, wherein the lower alcohol has a carbon number of from 1 to 5.

6. The method according to claim 2, wherein a weight ratio of the water to the lower alcohol is from 50/50 to 80/20 in a case where a mixed solution of water and the lower alcohol is used.

7. The method according to claim 3, wherein said sodium polyacrylate is contained in an amount of 0.0001 to 5% by weight.

8. The method according to claim 3, wherein said sodium polyacrylate has a weight-average molecular weight of from $200\times10^4$ to $2000\times10^4$.

9. The method according to claim 1, wherein the composition is applied by sprinkling or spraying to the house dust containing the allergen.

10. A method for inactivating an allergen comprising applying to a house dust containing the allergen a sheet impregnated with a composition, so that the allergen are inactivated, wherein
the composition consists of particles consisting of a titanium oxide having a photocatalytic activity, and optionally water, a lower alcohol or a mixture thereof, or sodium polyacrylate,
the titanium oxide consists of an anatase crystal form and 1 to 30 nm of an average primary particle size, and
the allergen is one or more selected from the group consisting of dead mites, feces of mites and pollens, and
wherein the composition does not include a titanium oxide having a rutile crystal form.

11. The method according to claim 10, wherein the composition consists of the particles consisting of the titanium oxide, and further the water, the lower alcohol or the mixture thereof.

12. The method according to claim 10 or 11, wherein the composition consists of the particles consisting of the titanium oxide, and sodium polyacrylate.

13. The method according to claim 10, wherein the titanium oxide is contained in an amount of 0.005 to 20% by weight.

14. The method according to claim 11, wherein the lower alcohol has a carbon number of from 1 to 5.

15. The method according to claim 11, wherein a weight ratio of the water to the lower alcohol is from 50/50 to 80/20 in a case where a mixed solution of water and the lower alcohol is used.

16. The method according to claim 12, wherein said sodium polyacrylate is contained in an amount of 0.0001 to 5% by weight.

17. The method according to claim 12, wherein said sodium polyacrylate has a weight-average molecular weight of from $200\times10^4$ to $2000\times10^4$.

18. The method according to claim 10, wherein the sheet is applied to the allergen by wiping a part, on which the house dust containing the allergen is accumulated, with the sheet.

19. The method according to claim 1, wherein the composition consists of the particles consisting of the titanium oxide, and further the lower alcohol.

20. The method according to claim 19, wherein the lower alcohol has a carbon number of from 1 to 5.

21. The method according to claim 1, wherein the composition consists of the particles consisting of the titanium oxide, the lower alcohol and the water, and
a weight ratio of the water to the lower alcohol is from 50/50 to 80/20.

22. The method according to claim 10, wherein the composition consists of the particles consisting of the titanium oxide and the lower alcohol.

23. The method according to claim 22, wherein the lower alcohol has a carbon number of from 1 to 5.

24. The method according to claim 10, wherein the composition consists of the particles consisting of the titanium oxide, the lower alcohol and the water,
the lower alcohol has a carbon number of from 1 to 5, and
a weight ratio of the water to the lower alcohol is from 50/50 to 80/20.

25. The method according to claim 10, wherein the sheet is a nonwoven fabric, a woven fabric, or a paper.

* * * * *